(12) United States Patent
Serraiocco et al.

(10) Patent No.: US 11,571,678 B2
(45) Date of Patent: Feb. 7, 2023

(54) HIGH PRESSURE STRIPPERS FOR USE IN UREA PLANTS

(71) Applicant: YARA INTERNATIONAL ASA, Oslo (NO)

(72) Inventors: Luigi Serraiocco, Skien (NO); Lino Giovanni Porro, Etterbeek (BE)

(73) Assignee: YARA INTERNATIONAL ASA, Oslo (NO)

( * ) Notice: Subject to any disclaimer, the term of this patent is extended or adjusted under 35 U.S.C. 154(b) by 188 days.

(21) Appl. No.: 17/055,501

(22) PCT Filed: May 16, 2019

(86) PCT No.: PCT/EP2019/062614
§ 371 (c)(1),
(2) Date: Nov. 13, 2020

(87) PCT Pub. No.: WO2019/219808
PCT Pub. Date: Nov. 21, 2019

(65) Prior Publication Data
US 2021/0187471 A1      Jun. 24, 2021

(30) Foreign Application Priority Data
May 16, 2018    (EP) .................... 18172538

(51) Int. Cl.
*B01J 19/24* (2006.01)
*B01J 19/00* (2006.01)
(Continued)

(52) U.S. Cl.
CPC ......... *B01J 19/2425* (2013.01); *B01J 19/006* (2013.01); *C07C 273/04* (2013.01);
(Continued)

(58) Field of Classification Search
CPC .................. B01J 19/2425; B01J 19/006; B01J 2219/00081; B01J 2219/00094; B01J 2219/00252; B01J 2219/00777; B01J 2219/185; B01J 2219/1943; B01J 2208/00221; B01J 2219/00076; B01J 19/0013; C07C 273/04; C07C 273/16;
(Continued)

(56) References Cited

FOREIGN PATENT DOCUMENTS

| CN | 107159081 A | 9/2017 |
|---|---|---|
| EP | 0002298 A2 | 6/1979 |

(Continued)

OTHER PUBLICATIONS

International Search Report and Written Opinion issued in International Application No. PCT/EP2019/062614, dated Aug. 2, 2019. 17 pages.

*Primary Examiner* — Huy Tram Nguyen
(74) *Attorney, Agent, or Firm* — Dilworth IP, LLC (57) ABSTRACT

A stripper for stripping a urea/carbamate mixture. The stripper comprises a shell and a plurality of tubes disposed within the shell. A shell-side space is provided between the tubes and the shell. A first heating fluid inlet, a second heating fluid inlet, and a heating fluid outlet are in fluid connection with the shell-side space. The second heating fluid inlet is disposed between the first heating fluid inlet and the heating fluid outlet. Related uses, systems, and methods are provided as well.

3 Claims, 8 Drawing Sheets

(51) Int. Cl.
*C07C 273/04* (2006.01)
*C07C 273/16* (2006.01)

(52) U.S. Cl.
CPC ... *C07C 273/16* (2013.01); *B01J 2219/00081* (2013.01); *B01J 2219/00094* (2013.01); *B01J 2219/00252* (2013.01); *B01J 2219/00777* (2013.01); *B01J 2219/185* (2013.01); *B01J 2219/1943* (2013.01)

(58) Field of Classification Search
CPC .......... F28F 9/167; F28F 9/0282; F28F 9/165; F28D 7/16
USPC ........................................................ 422/201
See application file for complete search history.

(56) References Cited

FOREIGN PATENT DOCUMENTS

| | | | | |
|---|---|---|---|---|
| WO | 0202535 A1 | 1/2002 | | |
| WO | WO-2011098335 A1 * | 8/2011 | ............... | B01D 1/06 |

* cited by examiner

HIGH PRESSURE STRIPPERS FOR USE IN UREA PLANTS

TECHNICAL FIELD

The present invention is in the field of urea manufacture, in particular in the field of high pressure strippers for decomposing carbamate and stripping ammonia in urea/carbamate mixtures from urea reactors in urea plants.

BACKGROUND

High Pressure Strippers are used in urea plants to concentrate urea, by removing the carbamate from a liquid urea/carbamate mixture. The urea/carbamate mixture is a solution of urea, ammonium carbamate, free ammonia and water, coming from a reactor in which urea is formed by the reaction of ammonia and $CO_2$ into ammonium carbamate (also referred to as carbamate) and subsequent dehydration of carbamate to produce urea. The conversion of carbamate into urea is, in practical terms, never complete and the solution leaving the urea reactor always comprises some carbamate and free ammonia.

A common way of removing carbamate and of concentrating the solution involves the use of a tube heat exchanger, called High Pressure Stripper, operating at a similar pressure to that of the Urea Reactor. Under the influence of the heat provided by a heating medium such as steam, the ammonium carbamate in the urea and carbamate mixture decomposes to form gaseous $NH_3$ and $CO_2$. These $NH_3$ and $CO_2$ gases are removed from the stripper. Accordingly, liquid urea is produced which is collected at the bottom of the stripper.

Two categories of high-pressure strippers exist: $CO_2$ strippers and self-strippers.

In $CO_2$ strippers, $CO_2$ is used as a stripping gas. It is fed to the bottom of the High Pressure Stripper and $NH_3$ and $CO_2$ produced during the decomposition of ammonium carbamate are entrained by the $CO_2$ stripping gas.

In self-strippers, no stripping gas is added to the stripper, but $NH_3$ and $CO_2$ formed during the decomposition of ammonium carbamate serve as the stripping gas.

The strippers comprise tubes and a shell, a top end, and a bottom end. During normal use, the top end is situated at the top of the stripper and the bottom end is situated at the bottom of the stripper. At the top end, a urea/carbamate mixture is distributed in the tubes and a gas mixture comprising stripping gas and entrained $NH_3$ and CO formed during carbamate decomposition leave the stripper. At the bottom end, the urea solution is collected. In the case of $CO_2$ strippers, $CO_2$ stripping gas is provided to the bottom end of the carbamate decomposer.

During normal operation, the tubes are installed substantially vertically. They enclose a tube-side space. A shell-side space is disposed between the tubes and the shell. The stripping gas and the urea/carbamate mixture run counter-current through the tube-side space while the urea/carbamate mixture is heated by means of a heating medium in the shell-side space, commonly steam. The urea/carbamate mixture flows into the tubes in a falling film pattern, while the gases rise in the inner part of the tubes.

It would be desirable to scale up such strippers in order to manufacture large volumes of urea in a cost-efficient way. Unfortunately, scaling up these strippers is not always easy and many unforeseen problems tend to occur during upscaling.

SUMMARY

The inventors identified two issues during upscaling of shell-and-tube strippers: severe tube corrosion and inefficient stripping. These issues are solved by way of the strippers, systems, and methods provided herein.

In particular, provided herein is a shell-and-tube stripper for stripping a urea/carbamate mixture, the stripper comprising a top end in fluid connection with a bottom end through a plurality of tubes disposed within a shell; the top end comprising an inlet for a urea/carbamate mixture and an outlet for a gas mixture comprising the stripping gas and one or more stripped compounds; the bottom end comprising an outlet for a urea/carbamate stream concentrated in urea and; wherein the stripper further comprises a first heating fluid inlet, a second heating fluid inlet, and a heating fluid outlet being in fluid connection with a shell-side space disposed between the plurality of tubes and the shell; the first heating fluid inlet being adjacently disposed to the top end of the stripper and the heating fluid outlet being adjacently disposed to the bottom end of the stripper; or the first heating fluid inlet being adjacently disposed to the bottom end of the stripper and the heating fluid outlet being adjacently disposed to the top end of the stripper; wherein the second heating fluid inlet is disposed between the first heating fluid inlet and the heating fluid outlet; wherein the second fluid inlet is positioned at a distance from the top end of the stripper that equals 35.0 to 75.0% of the distance between the top end and the bottom end of the stripper (100); and, wherein the stripper (100) comprises more than 3000 tubes (150).

In some embodiments, the first heating fluid inlet is adjacently disposed to the top end of the stripper and the heating fluid outlet is adjacently disposed to the bottom end of the stripper.

In some embodiments, the bottom end further comprises an inlet for a stripping gas.

In some embodiments, the second heating fluid inlet is positioned at a distance from the top end of the stripper that equals 35.0 to 70.0%, or 35.0 to 65.0%, or 40.0 to 60.0% of the distance between the top end and the bottom end of the stripper.

In some embodiments, the stripper comprises more than two heating fluid inlets, the more than two heating fluid inlets comprising the first heating fluid inlet, the second heating fluid inlet, and one or more further heating fluid inlets, the one or more further heating fluid inlets being positioned between the first heating fluid inlet and the heating fluid outlet.

In some embodiments, the stripper comprises more than 4000 tubes, or more than 5000 tubes, or more than 6000 tubes, or more than 7000 tubes.

In some embodiments, the stripper comprises a top and a bottom, wherein the top end is positioned at the top of the stripper and wherein the bottom end is positioned at the bottom of the stripper.

In some embodiments, the tubes have a length between 4.0 and 8.0 m, or a length between 5.0 and 7.0 m.

In some embodiments, the shell-side space comprises a plurality of baffles.

In some embodiments, the shell is cylindrical, and the shell has an outer diameter between 2.0 and 6.0 m, or between 3.0 and 5.0 m.

Further provided is a system for the production of urea comprising a carbamate condenser, a urea reactor, and a stripper as described herein.

Further provided is a system for the production of urea comprising a carbamate condenser, a urea reactor, and a stripper as described herein, the carbamate condenser being arranged to partially and exothermically transform ammonia and carbon dioxide into ammonium carbamate, and to partially convert the thusly formed ammonium carbamate to urea, thereby obtaining a condenser effluent comprising ammonium carbamate; the system being arranged to provide the condenser effluent to the urea reactor, the urea reactor being arranged to adiabatically convert at least a part of the ammonium carbamate in the condenser effluent into urea, thus obtaining a urea/carbamate mixture; the system being arranged to provide the urea/carbamate mixture to the stripper; the stripper being arranged to convert the urea/carbamate mixture into a urea/carbamate stream concentrated in urea and a gaseous stream comprising carbon dioxide and ammonia.

Further provided is a system for the production of urea comprising at least a combined carbamate condenser and urea reactor, the system further comprising a stripper as described herein, the combined reactor being arranged to partially and exothermally transform ammonia and carbon dioxide to ammonium carbamate; the combined reactor further being arranged to partially convert the ammonium carbamate into urea, thus obtaining a urea/carbamate mixture; the system being arranged to provide the urea/carbamate mixture to the stripper; the stripper being arranged to convert the urea/carbamate mixture into a urea/carbamate stream concentrated in urea and a gaseous stream comprising carbon dioxide and ammonia.

Further provided is a method for stripping a urea/carbamate mixture, the method comprising the steps: providing a stripper as described herein; providing the urea/carbamate mixture to the inlet for the urea/carbamate mixture; providing a heating fluid to the shell-side space by means of the first heating fluid inlet and by means of the second heating fluid inlet; contacting the urea/carbamate mixture and the stripping gas in a tube-side space disposed within the tubes, and heating the urea/carbamate mixture by means of the heating fluid, thereby obtaining a urea/carbamate stream concentrated in urea; extracting the urea/carbamate stream concentrated in urea at the outlet for the urea/carbamate stream concentrated in urea; extracting a gas mixture comprising one or more stripped compounds at the outlet for the gas mixture, the one or more stripped compounds comprising $NH_3$, $CO_2$, and water; extracting the heating fluid at the heating fluid outlet.

In some embodiments, the method additionally comprises the step of providing a stripping gas to the inlet for the stripping gas; and the gas mixture extracted at the outlet for the gas mixture further comprises the stripping gas.

In some embodiments, the heating fluid consists of steam.

Further provided is the use of a stripper as provided herein for stripping a urea-carbamate mixture.

DESCRIPTION OF THE FIGURES

The following description of the figures of specific embodiments of the invention is only given by way of example and is not intended to limit the present explanation, its application or use. In the drawings, identical reference numerals refer to the same or similar parts and features.

The following reference numerals are used in the description and figures: 100—stripper; 101—stripping gas feed; 102—tube for a urea/carbamate stream; 103—tube for stream comprising stripping gas and one or more stripped compounds; 104—tube for a urea/carbamate stream concentrated in urea; 110—top end (on top of the stripper during normal use); 111—inlet for a urea/carbamate mixture; 112—outlet for a gas mixture; 120—bottom end (at the bottom of the stripper during normal use); 121—inlet for stripping gas; 122—outlet for a urea/carbamate solution concentrated in urea; 130—shell-side space; 131—first heating fluid inlet; 132—second heating fluid inlet; 133—heating fluid outlet; 134—segmental baffles; 135—double segmental baffles; 136—disk-and-doughnut baffles; 140—tube-side space; 150—tube; 151—front tube sheet; 152—rear tube sheet; 153—corrosion area; 154—scaling area; 160—shell; 200—reactor; 201—tube for vapours of $NH_3$, $CO_2$, water, and inerts; 300—carbamate condenser; 301—tube for gaseous stream; 302—tube for carbamate solution stream; 400—scrubber; 401—tube for carbamate solution feed from downstream section; 402—tube for stream of inert gases; 500—heating fluid supply; 501—vapour generator; 502—connection to external heating fluid supply; 503—tube for heating fluid stream; 504—tube for cooled heating fluid stream; 600—high-pressure injector; 601—ammonia feed; 700—ferrule; 710—hole for urea/carbamate mixture; 720—hole for gas; 1000—high pressure section of a urea plant.

DESCRIPTION OF THE INVENTION

As used below in this text, the singular forms "a", "an", "the" include both the singular and the plural, unless the context clearly indicates otherwise.

The terms "comprise", "comprises" as used below are synonymous with "including", "include" or "contain", "contains" and are inclusive or open and do not exclude additional unmentioned parts, elements or method steps. Where this description refers to a product or process which "comprises" specific features, parts or steps, this refers to the possibility that other features, parts or steps may also be present, but may also refer to embodiments which only contain the listed features, parts or steps.

The enumeration of numeric values by means of ranges of figures comprises all values and fractions in these ranges, as well as the cited end points.

The term "approximately" as used when referring to a measurable value, such as a parameter, an amount, a time period, and the like, is intended to include variations of +/−10% or less, preferably +/−5% or less, more preferably +/−1% or less, and still more preferably +/−0.1% or less, of and from the specified value, in so far as the variations apply to the invention disclosed herein. It should be understood that the value to which the term "approximately" refers per se has also been disclosed.

All references cited in this description are hereby deemed to be incorporated in their entirety by way of reference.

Unless defined otherwise, all terms disclosed in the invention, including technical and scientific terms, have the meaning which a person skilled in the art usually gives them. For further guidance, definitions are included to further explain terms which are used in the description of the invention.

In the process of scaling up high-pressure shell-and-tube strippers for decomposition of urea-carbamate mixtures a remarkable corrosion pattern was observed. In particular, it was found that some tubes in high-pressure strippers for decomposition of urea-carbamate mixtures suffer from more severe corrosion than others. Without the invention being bound by any particular theory or mode of operation, it is believed that the corrosion-related issues are related to tube corrosion induced by ammonium carbamate at high temperature. It was further discovered that the corrosion-related issues can be explained by inhomogeneous heating of the tubes; ammonium carbamate causes more severe corrosion at higher temperatures such that inhomogeneous heating of the tubes causes inhomogeneous corrosion. During normal operation, the methods and devices disclosed herein improve temperature homogeneity in the liquid ammonium carbamate phase and as a consequence, lateral temperature variations are reduced.

The inventors discovered that such corrosion-related issues are related to inhomogeneous heating, i.e. to the presence of less-heated and more heated parts of the stripper. The inventors further discovered that the corrosion-related issues can be solved by means of the stripper designs disclosed herein. Thus, it can be ensured that the tubes in the strippers according to the present invention have an expected lifetime of around 20 to 30 years.

While the present invention was discovered in the context of scaling up strippers, it is not believed that the advantages offered by the present invention are anyhow limited to strippers of any particular size.

Provided herein is a shell-and-tube stripper for stripping a urea/carbamate mixture. The present invention is applicable to any kind of stripper for stripping urea/carbamate mixtures. In particular, it is applicable to both self-strippers and $CO_2$ strippers. In $CO_2$ strippers, $CO_2$ is used as a stripping gas. It is fed to the bottom of the High Pressure Stripper and $NH_3$ and $CO_2$ produced during the decomposition of ammonium carbamate are entrained by the $CO_2$ stripping gas. In self-strippers, no stripping gas is added to the stripper, but $NH_3$ and $CO_2$ formed during the decomposition of ammonium carbamate serve as the stripping gas. Accordingly, in some embodiments, the stripper is a $CO_2$ stripper, and the stripping gas is $CO_2$. Alternatively, in some embodiments, the stripper is a self-stripper, and the stripping gas is $NH_3$ and $CO_2$ generated by decomposition of the carbamate.

The term "carbamate" as used herein refers to ammonium carbamate. The term "urea/carbamate mixture" as used herein refers to a mixture comprising urea, ammonium carbamate, ammonia, and water. In some embodiments, the urea/carbamate mixture consists of 31 to 34 wt % urea, 32 to 35 wt % ammonium carbamate, 16 to 18 wt % ammonia, 0.1 to 0.3 wt % biuret, the balance being made up of water.

The expression "stripping a urea/carbamate mixture" as used herein refers to a process of decomposing ammonium carbamate comprised in the mixture to form ammonia and carbon dioxide. The formed ammonia and carbon dioxide are entrained by a stripping gas. Also, water comprised in the urea/carbamate mixture is at least partially entrained by the stripping gas as well.

The stripper is particularly useful as a high-pressure stripper in a urea plant that also contains a urea reactor. Such strippers commonly operate at a pressure which is similar to that of the urea reactor.

The stripper comprises a shell and a plurality of tubes disposed within the shell. In some embodiments, the tubes are vertically disposed within the shell. In some embodiments, the tubes have a length of more than 3.0 m, more than 4.0 m, or more than 5.0 m. In some embodiments, the tubes have a length between 4.0 and 8.0 m, or a length between 5.0 and 7.0 m. Preferably, the tubes have a length between 5.0 and 6.0 m.

The tubes preferably have an outer diameter between 20.0 and 40.0 mm.

In the case of a $CO_2$ stripper, the tubes preferably have an outer diameter between 20.0 and 40.0 mm, or between 25.0 and 35.0 mm.

In the case of a self-stripper, the tubes preferably have an outer diameter between 20.0 and 30.0 mm. In the case of a $CO_2$ stripper, the tubes preferably have an outer diameter between 30.0 and 35.0 mm.

In some embodiments, the stripper comprises more than 3000 tubes In some embodiments, the stripper comprises more than 4000 tubes, or more than 5000 tubes, or more than 6000 tubes, or more than 7000 tubes. In some embodiments, the stripper comprises 3000 to 7000 tubes, or 4000 to 6000 tubes, or 5000 to 7000 tubes, or 5000 to 10000 tubes.

Preferably, the tubes are made of stainless steel.

In a preferred mode of operation, the urea/carbamate mixture flows down as liquid film along the walls of the tubes, and the stripping gas flows upward through the centre of the tubes.

In some embodiments, the shell is cylindrical, and the shell has an outer diameter between 2.0 and 6.0 m, or between 3.0 and 5.0 m.

The stripper comprises a top end and a bottom end. During normal use, the top end of the stripper is positioned at the top of the stripper, and the bottom end is positioned at the bottom of the stripper. In other words, the stripper comprises a top and a bottom. During normal use, the top end is positioned at the top of the stripper, and the bottom end is positioned at the bottom of the stripper.

The tubes are disposed between the top end and the bottom end. A tube-side space is disposed within the tubes and a shell-side space is disposed between the tubes and the shell. The top end and the bottom end are in fluid connection with the tube-side space. In other words, the top end is in fluid connection with the bottom end through the plurality of tubes disposed within the shell. The shell-side space is separated from the top end, for example by means of a front tube sheet. The shell-side space is separated from the bottom end, for example by means of a rear tube sheet. When the top end is separated from the shell-side space by means of a front tube sheet, the fluid connection between the tubes and the top end is provided by means of perforations in the front tube sheet. When the bottom end is separated from the shell-side space by means of a rear tube sheet, the fluid connection between the tubes and the bottom end is provided by means of perforations in the rear tube sheet. Preferably the perforations in the front tube sheet and in the rear tube sheet are circular, the tubes are cylindrical, and the perforations have a diameter which equals the diameter of the tubes within a margin of error of less than 10.0%, 5.0%, 2.0%, or 1.0%.

The bottom end comprises an outlet for a urea/carbamate stream concentrated in urea. In some embodiments, this urea/carbamate stream concentrated in urea comprises unreacted ammonium carbamate, e.g. between 0.0 and 30.0 wt %, or between 10.0 and 20.0 wt %, or between 10.0 and 15.0 wt %, or between 15.0 and 25.0 wt % of ammonium carbamate.

In some embodiments, the urea/carbamate stream concentrated in urea comprises free ammonia, e.g. between 0.0 and 20.0 wt %, or between 0.5 and 1.0 wt %, or between 0.5 and 20 wt %, or between 10 and 15 wt % of free ammonia.

In some embodiments, the urea/carbamate stream concentrated in urea comprises both free ammonia and ammonium carbamate, for example in the above-specified concentrations.

In some embodiments, the stripper is a $CO_2$ stripper. When the stripper is a $CO_2$ stripper, its bottom end comprises an inlet for a stripping gas.

In some embodiments, the stripper is a self-stripper. When the stripper is a self-stripper, its bottom end does not comprise an inlet for a stripping gas. This notwithstanding, the bottom-end of self-strippers generally does comprise an inlet for a passivating gas stream. Preferably, air is used as a passivating gas stream. Note thought that the flow rates of the passivating air stream are so low that they do not contribute in any meaningful way to the stripping process itself. Typical flow rates of passivating air are 50 to 250 kg/hour, or 50 to 500 kg/hour of air.

The top end of the stripper comprises an inlet for a urea/carbamate mixture and an outlet for a gas mixture comprising the stripping gas and one or more stripped compounds. When a urea/carbamate mixture is stripped, the one or more stripped compounds comprise $NH_3$, $CO_2$, and water.

The stripper further comprises a first heating fluid inlet, a second heating fluid inlet, and a heating fluid outlet. The first heating fluid inlet, the second heating fluid inlet, and the heating fluid outlet are in fluid connection with the shell-side space.

The strippers provided herein suffer from reduced corrosion and provide better stripping efficiency, even when they are scaled up to a very large size. Without the invention being bound by any particular theory or mode of operation, it is believed that the reduced corrosion is due to improved homogeneity by which urea/carbamate mixture inside the tubes is heated. These mechanisms are elaborated on in the examples.

In some embodiments, the heating fluid is steam. In such embodiments, the heating fluid inlets are steam inlets, and the heating fluid outlet is a steam condensate outlet. Through a heating fluid outlet, steam condensate leaves the stripper's shell-side space.

In some embodiments, the first heating fluid inlet is adjacently disposed to the top end of the stripper, and the heating fluid outlet is adjacently disposed to the bottom end of the stripper. In other words, the first heating fluid inlet is preferably disposed at a distance from the top end of the stripper which is smaller than 20%, or 10.0%, or 5.0%, or 1.0% of the distance between the front and bottom ends of the stripper; and the heating fluid outlet is preferably disposed at a distance from the bottom end of the stripper which is smaller than 20%, or 10.0%, or 5.0%, or 1.0% of the distance between the front and bottom ends of the stripper.

In some embodiments, the first heating fluid inlet is adjacently disposed to the bottom end of the stripper and the heating fluid outlet is adjacently disposed to the top end of the stripper. The second heating fluid inlet is disposed between the first heating fluid inlet and the heating fluid outlet. In other words, the first heating fluid inlet is preferably disposed at a distance from the bottom end of the stripper which is smaller than 20%, or 10.0%, or 5.0%, or 1.0% of the distance between the front and bottom ends of the stripper; and the heating fluid outlet is preferably disposed at a distance from the top end of the stripper which is smaller than 20.0%, 15.0%, 10.0%, or 5.0%, or 1.0% of the distance between the front and bottom ends of the stripper.

However, preferably, the first heating fluid inlet is adjacently disposed to the top end of the stripper and the heating fluid is adjacently disposed to the bottom end of the stripper. In this way, steam condensate can be easily and efficiently removed from the shell-space side.

In some embodiments, the second heating fluid inlet is positioned at a distance from the top end of the stripper that equals 40.0 to 75.0% of the distance between the top end and the bottom end of the stripper. In some embodiments, the second heating fluid is positioned at a distance from the top end of the stripper that equals 35.0 to 75.0% of the distance between the top end and the bottom end of the stripper. In some embodiments, the second heating fluid is positioned at a distance from the top end of the stripper that equals 35.0 to 70.0%, or 35.0 to 65.0%, or 40.0 to 60.0% of the distance between the top end and the bottom end of the stripper.

In some embodiments, the second heating fluid inlet is positioned at a distance from the bottom end of the stripper that equals 40.0 to 75.0% of the distance between the top end and the bottom end of the stripper. In some embodiments, the second heating fluid is positioned at a distance from the bottom end of the stripper that equals 35.0 to 75.0%, or 35.0 to 70.0%, or 35.0 to 65.0%, or 40.0 to 60.0% of the distance between the top end and the bottom end of the stripper.

This further improves the homogeneity of the heat distributed to the tubes, which in turn reduces the occurrence of corrosion-related issues and improves the stripping efficiency.

In some embodiments, the stripper comprises more than two heating fluid inlets: the first heating fluid inlet, the second heating fluid inlet, and one or more further heating fluid inlets. The one or more further heating fluid inlets are positioned between the first heating fluid inlet and the heating fluid outlet.

In some embodiments, the stripper comprises one or more groups of heating fluid inlets. A group of heating fluid inlets consists of two or more heating fluid inlets which are positioned at the same longitudinal position in the stripper. The expression "longitudinal position in the stripper" refers to the position in the direction along which the tubes are positioned. During normal operation, the stripper is positioned upright and the tubes are arranged vertically, such that the longitudinal position of a steam inlet in the stripper corresponds to the height at which the steam inlet is positioned.

When objects are said to be vertically oriented, reference is made to the orientation of their longitudinal axis. It shall be understood that this orientation may have a certain deviation from the vertical axis. Preferably, this deviation is less than 1.0°, or less than 0.5°. More preferably, the deviation is less than 0.1°.

In some embodiments, the first heating fluid inlet is replaced by a first group of heating fluid inlets.

In some embodiments, the second heating fluid inlet is replaced by a second group of heating fluid inlets.

In some embodiments, the heating fluid outlet is replaced by a group of heating fluid outlets.

In some embodiments, the stripper comprises two or more groups of heating fluid inlets positioned between the first group of heating fluid inlets and the group of heating fluid outlets, for example 3, 4, 5, 6, 7, or 8 groups of heating fluid inlets.

In some embodiments, the heating fluid inlets, or the groups of heating fluid inlets, are evenly spaced. The term "evenly spaced" indicates that the distances between adjacent heating fluid inlets or groups of heating fluid inlets deviate less than 20.0%, less than 10.0%, less than 5.0%, less than 1.0%, or less than 0.10% from the average distance between adjacent heating fluid inlets.

These particular arrangements of heating fluid inlets and/or outlets further improve the homogeneity by which heat is provided to the tubes.

In some embodiments, the shell-side space comprises a plurality of baffles, for example disk-and-doughnut baffles. Disc-and-doughnut baffles comprise alternating disk-shaped baffles and ring-shaped baffles. The ring-shaped baffles comprise a central hole; the disk-shaped baffles do not. In other words, the disk-shaped baffles are shaped as solid disks. In some embodiments, the diameter of the central hole of the ring-shaped baffles is smaller than the diameter of the disk-shaped baffles.

Figure 8:
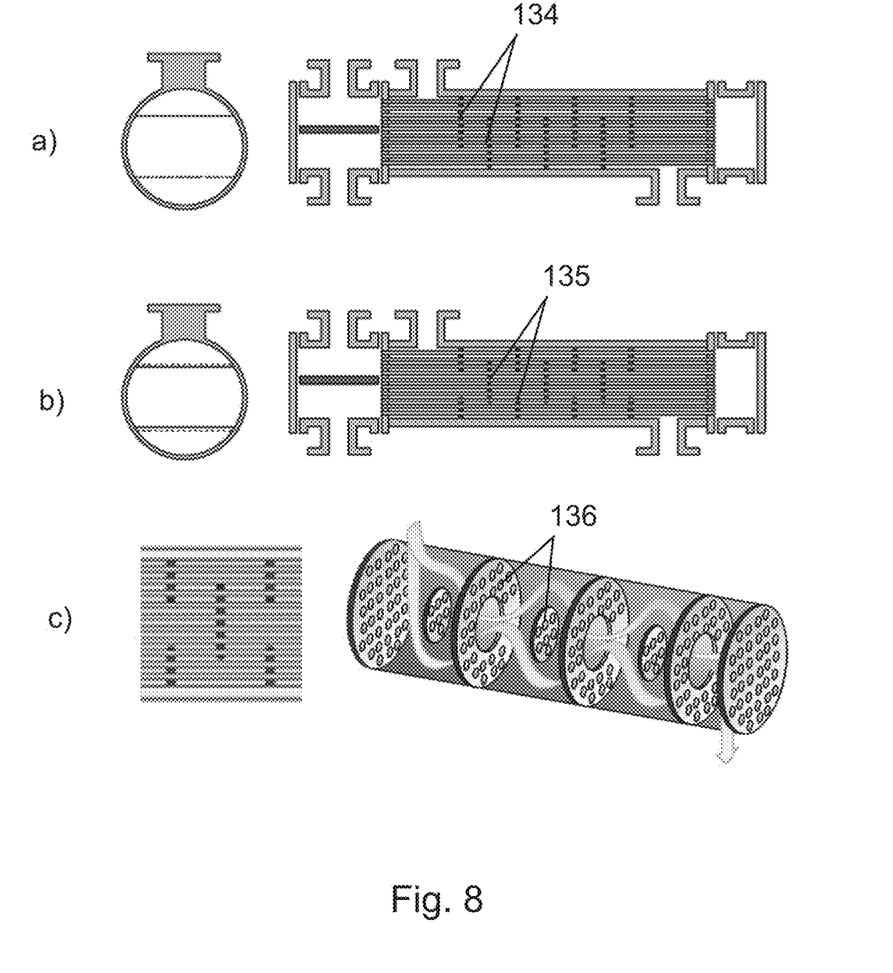
FIG. 8 shows several exemplary baffle types.

Other suitable types of baffles are segmental, and double segmental, as can be seen in FIG. 8.

The rate of corrosion of the tubes by the ammonium-carbamate mixture significantly is significantly influenced by the type of baffles which is used. For example, for disk-and-doughnut baffles, the higher heat transfer occurs for tubes placed in proximity of the edges of the disks and especially doughnut baffles.

The above types of baffles are effective at reducing the amount of corrosion in the tubes in conjunction with the use of a two heating fluid inlets as described above.

This is especially the case for big (sizeable) strippers.

In some embodiments, the baffles are perforated, i.e. they comprise a plurality of perforations. In some embodiments, the perforations are circular to accommodate the tubes. Preferably, the perforations have a diameter which is larger than the outer diameter of the tubes. For example, the perforations have a diameter which is 1.0% to 10.0% larger, or 2.0 to 5.0%, or 1.0 to 3.0% larger than the diameter of the tubes.

In some embodiments, the baffles are evenly spaced, i.e. the distance between adjacent baffles is constant within a margin of error of 25.0%, 15.0%, 10.0%, 5.0%, 1.0%, or 1.0%.

In some embodiments, the top end of the stripper is separated from the tubes by means of a front tube sheet comprising a plurality of ferrules. Each ferrule is a liquid divider and is coupled with the tubes. The ferrules are configured to evenly distribute a urea/carbamate mixture through each tube via holes in the ferrule. Preferably, the holes are provided in the bottom part of the ferrule. Also, the ferrules comprise one or more holes, preferably in their top part, which allow releasing gas flow to the top end of the stripper.

Further provided is the use of a stripper as described above for stripping a urea-carbamate mixture.

Further provided is the use of a stripper as described above for improving the stripping efficiency and/or for reducing tube corrosion while stripping urea/carbamate mixtures.

Further provided herein is a system for the production of urea. The system comprises a carbamate condenser, a urea reactor, and a stripper.

The stripper is a shell-and-tube stripper and has been described above. In particular, the stripper may be a $CO_2$ stripper or a self-stripper as described above.

Various types of systems for the production of urea are known in the art, see e.g. the chapter on urea in Jozef H. Meessen and Harro Petersen, Ullmann's Encyclopedia of Industrial Chemistry, Wiley-VCH Verlag GmbH & Co., 2005.

Exemplary embodiments of a system for the production of urea are described next. In some embodiments, the urea reactor and the carbamate condenser are separate reactor vessels. Alternatively, the urea reactor and the carbamate condenser are realised as an integrated urea reactor and the carbamate condenser. These two embodiments are discussed separately.

When the carbamate condenser and the urea reactor are separate reactor vessels, the carbamate condenser is arranged to partially and exothermically transform ammonia and carbon dioxide into ammonium carbamate, and the carbamate condenser partially converts the thusly formed ammonium carbamate to urea. Thus, a condenser effluent is obtained. The urea reactor is arranged to adiabatically convert at least a part of the ammonium carbamate in the condenser effluent into urea. Thus, a urea/carbamate mixture is obtained. The system is arranged to provide the urea/carbamate mixture to the stripper. The stripper is arranged to convert the urea/carbamate mixture into a urea/carbamate stream concentrated in urea and a gaseous stream comprising carbon dioxide and ammonia.

When the system comprises a combined reactor that serves both as carbamate condenser and urea reactor, the combined reactor is arranged to partially and exothermally transform ammonia and carbon dioxide to ammonium carbamate. In addition, the combined reactor is further arranged to partially convert the ammonium carbamate into urea. Thus, a urea/carbamate mixture is obtained. The system is arranged to provide the urea/carbamate mixture to the stripper and the stripper is arranged to convert the urea/carbamate mixture into a urea/carbamate stream concentrated in urea and a gaseous stream comprising carbon dioxide and ammonia.

Further provided is a method for stripping a urea/carbamate mixture. Additionally or alternatively, this method can be stated to be a method for reducing corrosion in tubes of strippers for decomposing urea/carbamate mixtures and/or for improving stripping efficiency when stripping urea/carbamate mixtures.

The method comprises the step of providing a stripper. The stripper is a stripper as described above. Preferably, the stripper is positioned such that the tubes are disposed vertically within the shell. Also, the stripper is preferably positioned such that the top end is on top of the stripper, and the bottom end is at the bottom of the stripper. The urea/carbamate mixture is provided to the inlet for the urea/carbamate mixture.

When a $CO_2$ stripper is used, a stripping gas (i.e. $CO_2$), is provided to the inlet for the stripping gas. When a self-stripper is used, $CO_2$ and $NH_3$ formed during the decomposition of ammonium carbamate serves as the stripping gas. Note that as mentioned above, self-strippers do typically comprise an inlet for passivating air for the purpose of corrosion reduction, but the flow rates of passivating air are insufficient to contribute to the stripping process in a meaningful way.

A heating fluid is provided to the shell-side space by means of 2 or more heating fluid inlets. The urea/carbamate mixture and the stripping gas are contacted in the tubes. In particular, the urea/carbamate mixture flows as a falling film along the inner walls of the tubes. The stripping gas flows upward in the tube-side space.

The urea/carbamate mixture is heated by means of the heating fluid. Under influence of heat provided by the heating fluid, ammonium carbamate in the urea/carbamate decomposes to form gaseous ammonia and carbon dioxide. As ammonium carbamate in the urea/carbamate mixture decomposes a urea/carbamate stream concentrated in urea is obtained. The urea/carbamate stream concentrated in urea is extracted at the outlet for the urea/carbamate stream concentrated in urea.

A gas mixture comprising the one or more stripped compounds is extracted at the outlet for the gas mixture. When a $CO_2$ stripper is used, this gas mixture comprises the stripping gas as well. The heating fluid is extracted from the shell-side space by means of a heating fluid outlet.

These methods effectively allow better stripping urea/carbamate mixtures while reducing corrosion of strippers.

In some embodiments, the temperature of the tubes is constant along any radial cross section through the stripper. The term "radial cross section through the stripper" refers to a cross section through the stripper in a plane which is perpendicular to the tubes. In other words, a radial cross section is a lateral cross section. In some embodiments, the temperature of the tubes is constant along any radial cross section through the stripper within a margin of error of less than 10° C., less than 5° C., less than 2° C., or less than 1° C. A constant temperature along radial cross sections through the stripper ensures uniform heat transfer to the tubes. As a result, such radially constant temperatures reduce corrosion of the stripper's tubes.

In some embodiments, the pressure in the shell-side space is between 10.0 and 30.0 bar g, preferably between 16.0 and 24.0 bar g.

The mass flow rate of the heating fluid depends on the capacity of the stripper. In some embodiments, the mass flow rate of the heating fluid is between 10.0 and 60.0 kg/s, between 20.0 and 50.0 kg/s, or between 30.0 and 40.0 kg/s.

In some embodiments, the heating fluid comprises steam. Preferably, the heating fluid essentially consists of steam. In other words, the heating fluid preferably comprises at least 99.0 wt % steam, or at least 99.9 wt % steam. The symbol wt % indicates that the composition of the heating fluid is expressed as a weight percentage, i.e. as the ratio in percent of the mass flow rate of steam comprised in the heating fluid and the mass flow rate of the entire heating fluid.

In some embodiments, the heating fluid has a density between 7.0 and 13.0 kg/m³, or between 8.5 and 12.0 kg/m³.

EXAMPLES

Example 1

Figure 1:
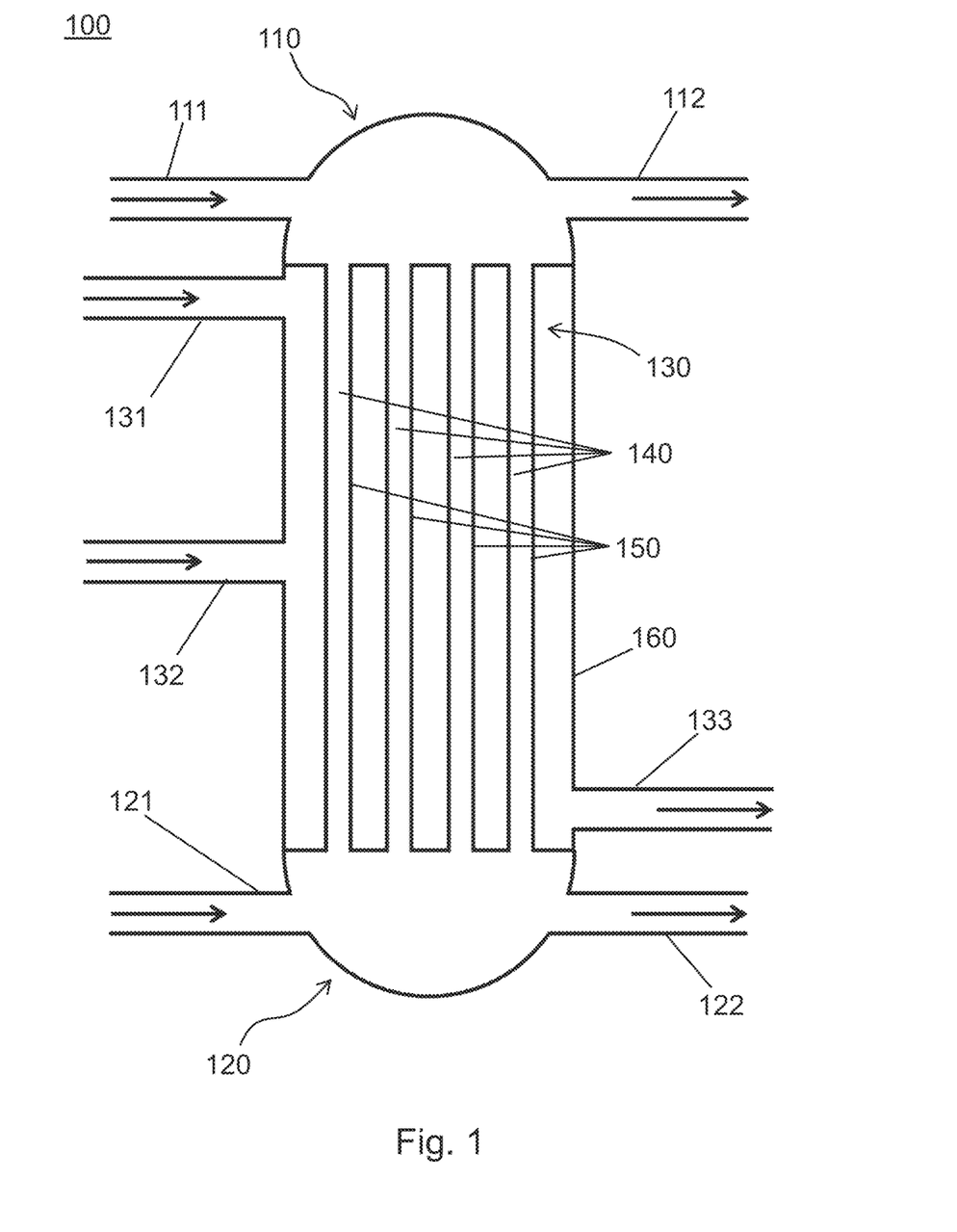
FIG. 1 shows a $CO_2$ stripper (100).

In a first example, reference is made to FIG. 1 which shows a stripper (100) as provided herein. In particular, the stripper (100) is a $CO_2$ stripper. The stripper (100) comprises a shell (160) and a plurality of tubes (150) which are disposed within the shell (160). Also, the stripper (100) comprises a top end (110) and a bottom end (120). The tubes (150) are disposed between the top end (110) and the bottom end (120). A tube-side space (140) is disposed within the tubes (150). A shell-side space (130) is disposed between the tubes (150) and the shell (160). The shell-side space (130) is separated from the top end (110) and the bottom end (120). The top end (110) and the bottom end (120) are in fluid connection with the tube-side space (140).

The bottom end (120) comprises an outlet (122) for a urea/carbamate stream concentrated in urea and an inlet (121) for a stripping gas.

The top end (110) comprises an inlet (111) for a urea/carbamate mixture and an outlet (112) for a gas mixture that comprises the stripping gas and one or more stripped compounds.

The stripper (100) further comprises a first heating fluid inlet (131), a second heating fluid inlet (132), and a heating fluid outlet (133). The first heating fluid inlet (131), the second heating fluid inlet (132), and the heating fluid outlet (133) are in fluid connection with the shell-side space (130). Also, the first heating fluid inlet (131) is adjacent to the top end (110) of the stripper (100). The heating fluid outlet (133) is adjacent to the bottom end (120) of the stripper (100). The second heating fluid inlet (131) is positioned halfway between the first heating fluid inlet (132) and the heating fluid outlet (133).

The tubes (150) have a length of 6.0 m and an outer diameter of 31.0 mm. The stripper has a cylindrical shell with a diameter of 3.1 m.

Example 2

Figure 2:
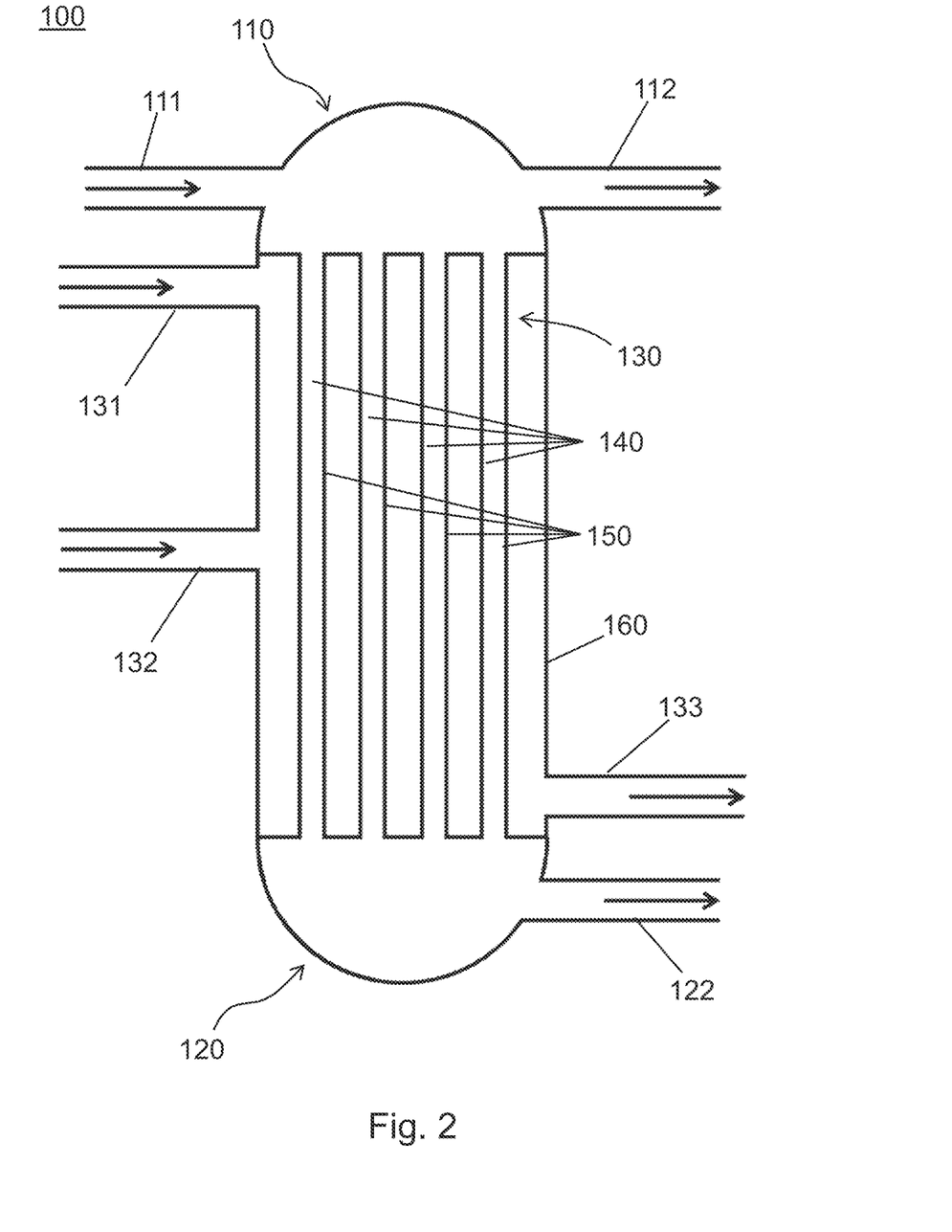
FIG. 2 shows a self-stripper (100).

In a second example, reference is made to FIG. 2 which shows a stripper (100) as provided herein. In particular, the stripper (100) is a self-stripper. The construction of the stripper (100) is similar to that of example 1 with a few differences.

In particular, the self-stripper does not comprise a stripping gas inlet at its bottom end: $NH_3$ and $CO_2$ formed during the decomposition of ammonium carbamate serve as the stripping gas in self-strippers such that there is no need for a stripping gas inlet.

Also, the tubes of the self-stripper are thinner than those of the $CO_2$ stripper of example 1. In particular, the tubes of the self-stripper have an outer diameter of 25 mm.

Example 3

In a third example, an exemplary method for operating the stripper (100) of example 1 is discussed. In this method, the stripper (100) is positioned vertically, and the top end (110) is positioned at the top of the stripper, and the bottom end (120) is positioned at the bottom of the stripper (100).

The method involves providing a mixture comprising urea and ammonium carbamate to the inlet (111) for the urea/carbamate mixture, and providing $CO_2$, the stripping gas, to the inlet (121) for the stripping gas.

The stripping gas and the urea/carbamate mixture flow in counter-current through the tubes (150). Concurrently, the urea/carbamate mixture is heated and the ammonium carbamate comprised in the urea/carbamate mixture decomposes to form gaseous $NH_3$ and $CO_2$ which are entrained by the stripping gas. Thus, a urea/carbamate stream concentrated in urea is formed in the tubes (150). This stream flows downward to the bottom end (120) where it is extracted by means of the outlet (122) for a urea/carbamate stream concentrated in urea.

Steam is used as a heating fluid, and is provided to the shell-side space (130) by means of the first heating fluid inlet (131) and by means of the second heating fluid inlet (132). The second heating fluid inlet (132) is positioned halfway between the first heating fluid inlet (131) and a heating fluid outlet (133). The steam has an operating pressure of about 18 bar (absolute pressure), it has a mass flow rate of 36 kg/sec, and a vapour density of 9 kg/m$^3$.

Condensed steam is extracted from the shell-side space (130) through the heating fluid outlet (133). In traveling from the heating fluid inlets (131,132) to the heating fluid outlet (133), the steam travels through the shell-side space (130) and heats the tubes (150) and their content, which allows the aforementioned decomposition of ammonium carbamate to form $NH_3$ and $CO_2$. The provision of the two heating fluid inlets (131,132) ensures homogeneous heating of the tubes (150) and their content which in turn results in improved stripper efficiency and less corrosion of the tubes.

Example 4

In a fourth example, an exemplary method for operating the stripper (100) of example 2 is discussed. In particular, its operation is similar to that of the stripper of example 1, except that no stripping gas is provided to the bottom end. Instead, $NH_3$ and $CO_2$ formed during the decomposition of ammonium carbamate serve as the stripping gas.

Example 5

Figure 3:
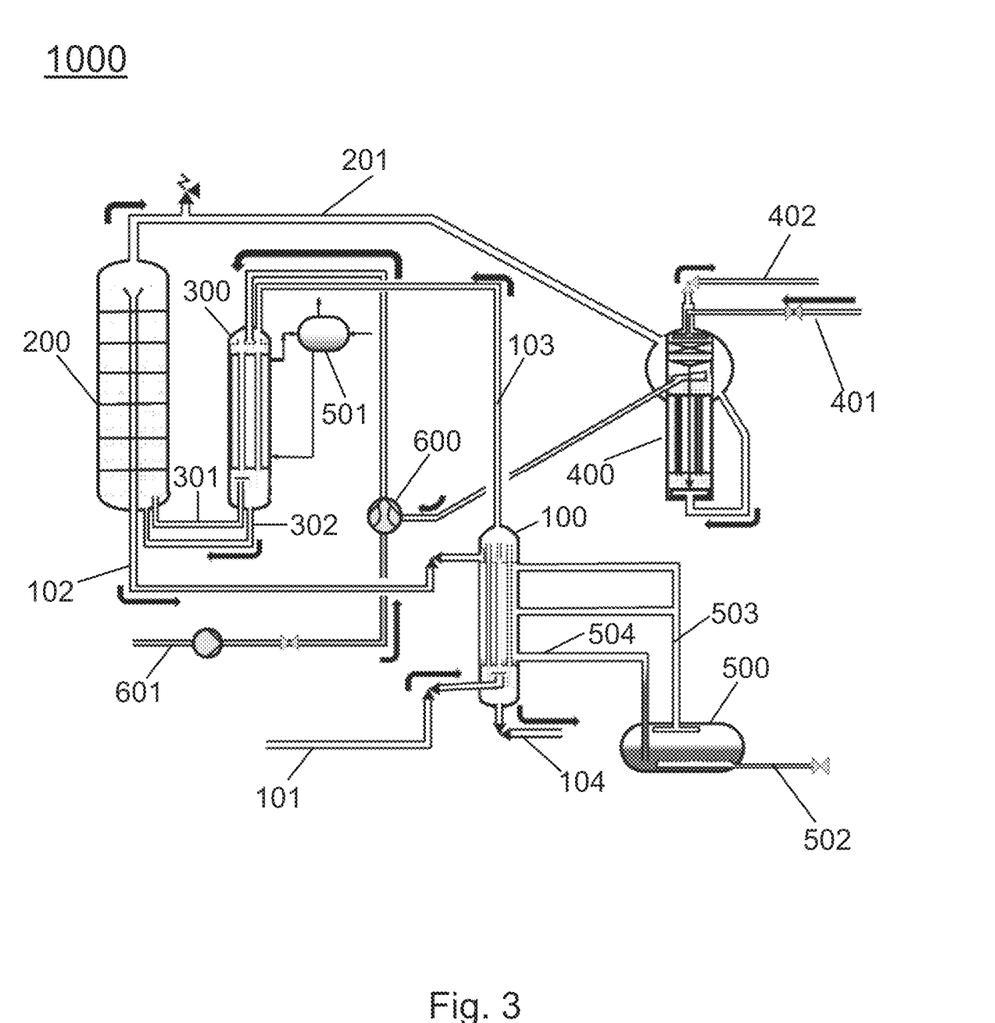
FIG. 3 shows an example of a high-pressure section of a specific type of urea plant in which the presently disclosed technology can be used.

In a further example, reference is made to FIG. 3 which shows selected parts of a urea plant (1000). The urea plant comprises a stripper (100) as described in example 1, a reactor (200) for converting ammonium carbamate into urea, a carbamate condenser (300) for forming ammonium carbamate, and a scrubber (400) for condensing $NH_3$ and $CO_2$ vapours coming from the reactor and the carbamate condenser. The scrubbing liquid is a carbamate solution fed by a tube (401) from a downstream section.

A stripping gas feed (101) is in fluid connection with the inlet (121) for stripping gas of the stripper (100). A tube (104) for a urea/carbamate stream concentrated in urea is in fluid connection with the outlet (122) of the urea/carbamate stream concentrated in urea of the stripper (100). The stripper (100) comprises a shell-side space—see FIG. 1 (130)—which comprises two heating fluid inlets and a heating fluid outlet—see FIG. 1 (131,132,133). The heating fluid inlets are in fluid connection with a branching tube for a heating fluid stream (503). The heating fluid outlet is in fluid connection with a tube for a cooled heating fluid stream (504). The branching tube for a heating fluid stream (503) and the tube for a cooled heating fluid stream (504) are in fluid connection with a heating fluid supply (500), which in turn is in fluid connection with a connection (502) to an external heating fluid supply. The stripper (100) is further in fluid connection with a tube (102) for a urea/carbamate stream. This tube (102) delivers the urea/carbamate stream from a reactor (200) which transforms ammonium carbamate into urea. The reactor in turn is provided with ammonium carbamate by a carbamate condenser (300) via a tube (302) and with gaseous $NH_3$, $CO_2$, water, and inerts via another tube (301). Heat generated by carbamate formation in the carbamate condenser (300) is extracted by means of steam and a vapour supply (501).

Example 6

In a further example, reference is made to FIGS. 4, 5, 6, and 7 which illustrate some of the challenges which are overcome by way of the systems and methods according to the present invention. In particular, the present systems and methods offer improved stripper life and enhanced stripper efficiency. The present example illustrates these issues for a specific $CO_2$ stripper. However, similar corrosion issues are expected to occur in other types of strippers as well when inhomogeneous heating occurs though the precise corrosion pattern is expected to depend on the specific stripper morphology. One example of a different type of stripper in which similar corrosion issues are expected is a self-stripper.

Figure 4:
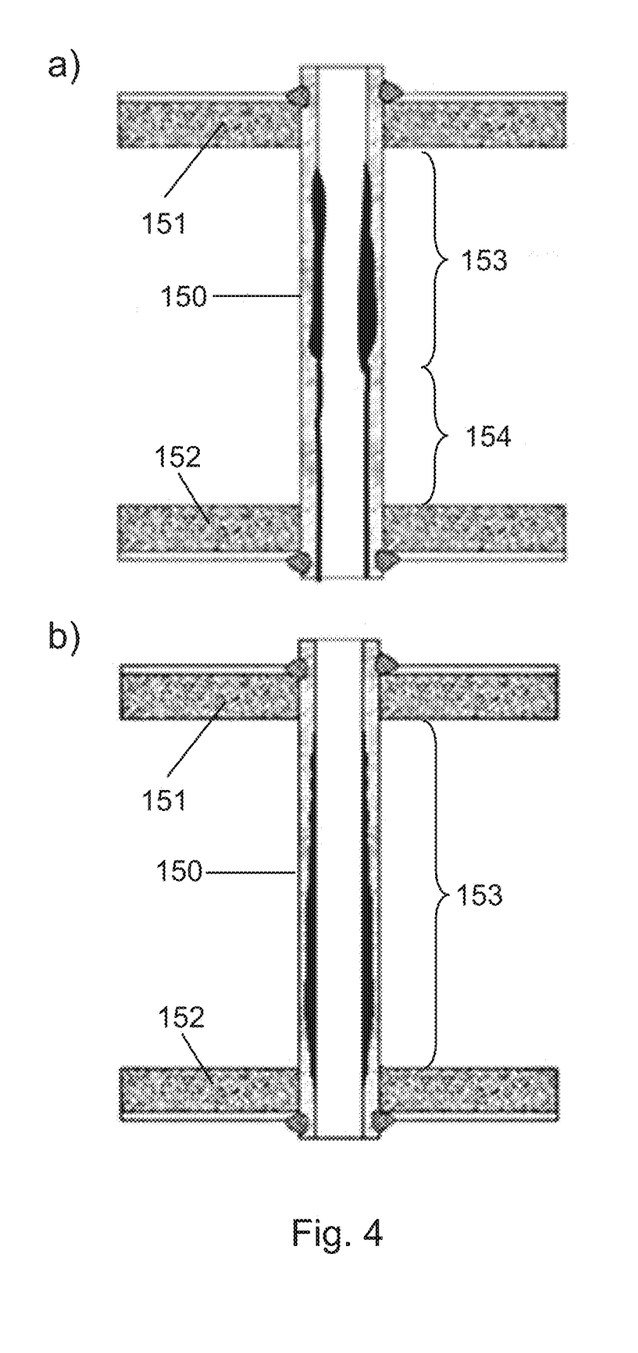
FIG. 4 shows two corrosion patterns which concurrently occur in the tubes of prior art shell-and-tube strippers for stripping urea/carbamate mixtures. In some modes of operation, the corrosion pattern shown in FIG. 4a occurs in $CO_2$ strippers and that shown in FIG. 4b occurs in self-stripping strippers.

FIG. 4 shows two corrosion patterns that particularly occur in sizable $CO_2$ strippers with only one heating fluid inlet, with stainless steel tubes, and in which $CO_2$ is used as a stripping gas for stripping a urea/carbamate solution. More specifically, the corrosion pattern was observed in shell-and-tube strippers which have tubes of 6 m high, have a shell diameter of about 3 m, have disk-and-doughnut baffles installed in the shell-side space, and comprise about 5000 tubes (150).

The corrosion type also depends on whether the stripper is a $CO_2$ stripper or a self-stripping stripper. Indeed, the corrosion pattern shown in FIG. 4 a) was found to commonly occur in small-diameter $CO_2$ strippers and that shown in FIG. 4b was found to commonly occur in small-diameter self-stripping strippers. In the context of the present invention, both $CO_2$ strippers and self-stripping strippers are shell-and-tube strippers.

Shell-and-tube strippers comprise a front tube sheet (151) which is positioned above and at the top end of the tubes. It separates a shell-side space comprising disk-and-doughnut baffles from the stripper's top end. The front tube sheet (151) also allows a urea/carbamate mixture to flow down as liquid film along the internal wall of the tubes (150). It also allows a gas mixture comprising $CO_2$ and $NH_3$ to exit the tubes (150).

The shell-and-tube strippers also comprise a rear tube sheet (152) which is positioned below and at the bottom end of the tubes. It separates the shell-side space from the stripper's bottom end. The rear tube sheet (152) also allows a urea/carbamate stream concentrated in urea to exit the tubes (150) and in $CO_2$ stripper it allows the $CO_2$ stripping gas to enter the tubes (150).

Figure 5:
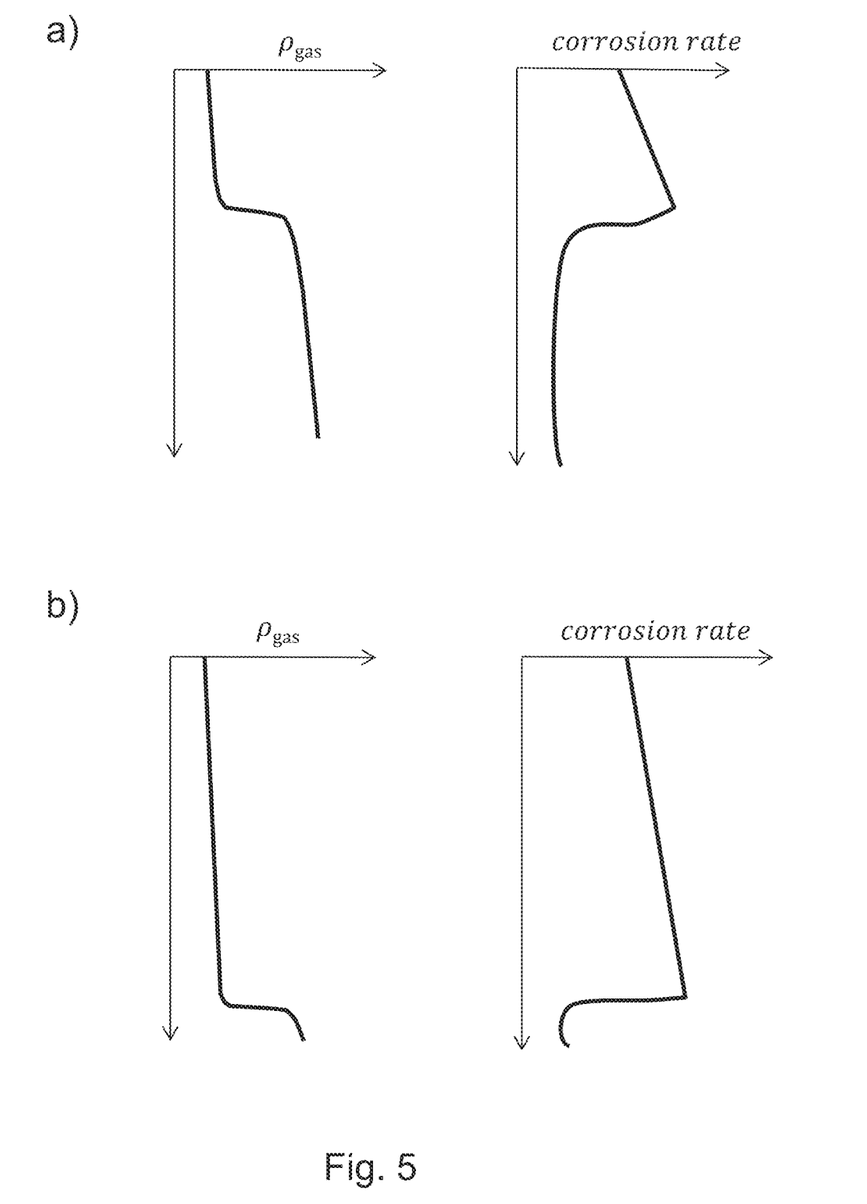
FIG. 5 shows gas densities and corrosion rates which concurrently occur in the tubes of prior art shell-and-tube strippers for stripping urea/carbamate mixtures.

These strippers feature different corrosion patterns in the outer and inner tubes of the stripper. The inner tubes approximately cover the cross-section of the disk baffles, and the outer tubes approximately cover the cross-section of the doughnut baffles. The corrosion pattern in the outer tubes is shown in FIG. 4, panel a). The corrosion pattern in the inner tubes is shown in FIG. 4, panel b). The corrosion rate in the outer tubes is schematically shown in FIG. 5, panel a), right-hand graph. The corrosion rate in the inner tubes is schematically shown in FIG. 5, panel b), right-hand graph.

In the outer tubes, both a corrosion area (153) and a scaling area (154) are present. Conversely, in the inner tubes, only a corrosion area (153) is present. In the corrosion areas, corrosion of the tubes occurs. In the scaling area (154), no corrosion occurs but iron scale is deposited. Although the corrosion area in the outer tubes extends only along part of the length of the tubes, the corrosion is much more severe in the corrosion area (153) of the outer tubes. The useful life of strippers is limited by the rate of corrosion of the tubes. Therefore, if the rate of corrosion occurring in the outer tubes (150) could be avoided, the extent of corrosion after a certain period in operation would be reduced, and consequently the useful life of the strippers could be increased.

Without restricting the present invention to any particular mode of operation, it is believed that the occurrence of the inhomogeneous corrosion in prior art $CO_2$ strippers for stripping ammonium carbamate from urea/carbamate streams can be explained as follows. During normal operation of prior art strippers, a urea/carbamate mixture flows down the internal wall of the tubes (150) as a falling film pattern, and it is heated by means of steam provided to the shell-side space. Under influence of the heat, the ammonium carbamate in the urea/carbamate mixture decomposes to form gaseous $NH_3$ and $CO_2$, which flow upward along with the stripping gas. Thus ammonium carbamate is gradually decomposed.

In arriving at the present invention, it was realised that the presence of iron scales in the lower part of the outer tubes, i.e. the scaling part (154), indicates that in the scaling part, the liquid phase consists mainly of urea, residual carbamate, free $NH_3$ and water. In other words, a large portion of the ammonium carbamate has decomposed, thereby leaving a liquid phase essentially consisting of urea, residual carbamate, free $NH_3$ and water that flows down the tube walls at the scaling part (154): Iron (Fe) is significantly less soluble in urea than in ammonium carbamate. Conversely, the centre tubes do not have a scaling part, which indicates that ammonium carbamate has not entirely been decomposed.

It was further realised that the rate at which the ammonium carbamate is decomposed increases with an increasing amount of heat which is provided to the tubes (150). Accordingly, the observation that ammonium carbamate decomposes closer to the top end of the stripper in the outer tubes indicates more intense heating in the outer tubes compared to the inner tubes. Because the heat is provided by means of steam flowing on the shell-side space of the stripper, the amount of heat is determined by the flow of steam. Therefore, the provision of more heat to the outer tubes compared to the inner tubes is related to the flow of steam in the shell-side space of the stripper. The inventors thus discovered that inhomogeneous flow of steam in the shell-side space of the stripper is the cause for the observed increased corrosion rate in the outer tubes compared to the inner tubes.

It was additionally discovered that the inhomogeneous heating of the tubes results in inefficient operation of strippers related to inhomogeneous $CO_2$ stripping gas distribution over the tubes. In particular, it was found that under typical operating conditions of prior art shell-and-tube strippers featuring a single steam inlet and disk-and-doughnut baffles in the shell-side space, the gas flow rate through the less-heated inner tubes is significantly higher than the gas flow rate through the more heated outer tubes. Inhomogeneous stripping gas flow leads to process inefficiencies such as the inhomogeneous stripping of the carbamate in the tubes and consequently an ineffective decomposition of ammonium carbamate in the stripper.

Figure 7:
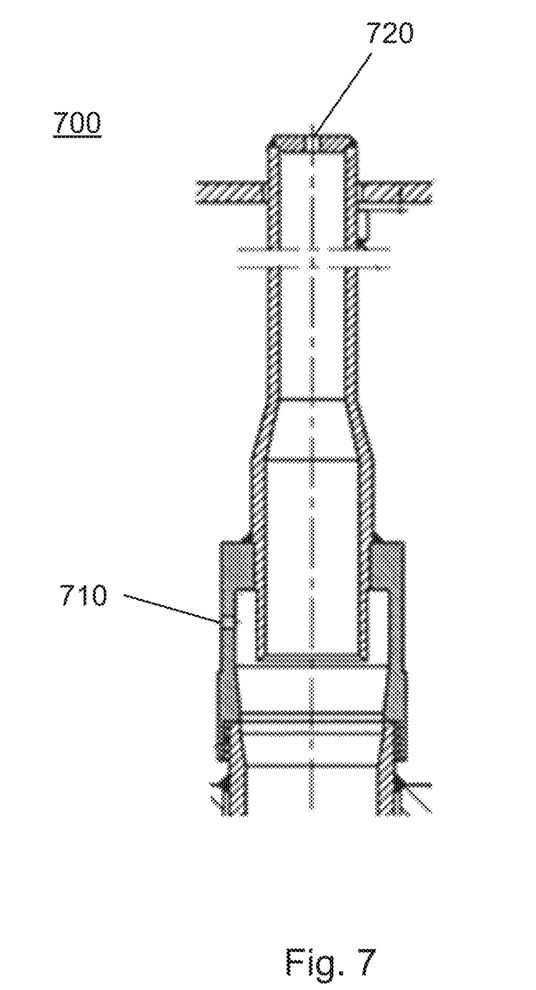
FIG. 7 shows an example of a ferrule (700).

Liquid dividers (so called ferrules, an example of which is shown in FIG. 7), are installed in the stripper front head and coupled with tubes in the front tube sheet in order to assure an even distribution of the urea/carbamate mixture though each tube via holes (710) in the bottom part of the ferrule. Also, one or more holes (720) in the liquid divider top part are installed to release the gas flow to the stripper top end. The stripping gas flow is determined by a combination of hydrodynamic and hydrostatic effects. The hydrodynamic effects correspond to the pressure drop across the one or more holes (720) in the top liquid dividers (so called ferrules), and can be written as $\Delta p = 0.5 \rho v^2$, with $\Delta p$ pressure drop, $\rho$ fluid density, and $v$ fluid velocity.

For typical operating conditions, the hydrodynamic pressure drop across the tubes is about 250 Pa. The hydrostatic effect corresponds to the pressure effect due to the gas density along the height of the tubes, and, for a given pressure, can be written as $\Delta p = \Delta \rho g h$. The hydrostatic pressure drop in the stripper that was described above is estimated to be about 5500 Pa. Accordingly, the hydrostatic effect dominates, and it is therefore mostly responsible for the stripping gas flow distribution across the tubes. Therefore, any possible imbalance in stripping gas flow between the tubes caused by differences in hydrostatic pressure drop across the tubes cannot be compensated by changing the hydrodynamic pressure drop across the hole on top of the ferrules. The pressure drop across the hole might be changed by changing the size of the hole in the ferrule. By reducing the hole size the pressure drop would increase and vice versa.

It was discovered that in more heated tubes, carbamate decomposition and the accompanying release of $CO_2$ and $NH_3$ occurs in the top parts of the tubes, i.e. near the top end, e.g. in the upper 50% of the tubes. Therefore, the partial pressure of $NH_3$ at the top of the tubes is high, whereas the partial pressure of $NH_3$ in the bottom part of the tubes is low. The stripping gas is $CO_2$, and under the same conditions, $NH_3$ has a lower density than $CO_2$. Because the gas flows upward, the $NH_3$ concentration is highest in the top part of the tubes. Therefore, the top part of the tubes has a lower specific density than the bottom part of the tubes. This is illustrated in FIG. 5, panel a). This figure shows that the tubes comprise three regions: a lower region featuring a higher gas density and lower corrosion rate, a transition region in which the gas density and the corrosion rate suddenly change, and an upper region which has a higher corrosion rate and a lower gas density. In particular, going up the tubes, the first region the gas encounters is the lower region. In the lower region, the gas density gradually decreases as the gas is heated while it travels up the tubes. In the transition region the gas density suddenly decreases due to the decomposition of ammonium carbamate and the resulting release of ammonia gas. In the upper region, the gas density gradually decreases as the gas is further heated, and the corrosion rate is high because the tube walls are in contact with an intensely heated urea/carbamate solution. Indeed, the corroded thickness of the tube increases moving downwards within the upper region, as the solution gets warmer while moving downwards.

Figure 6:
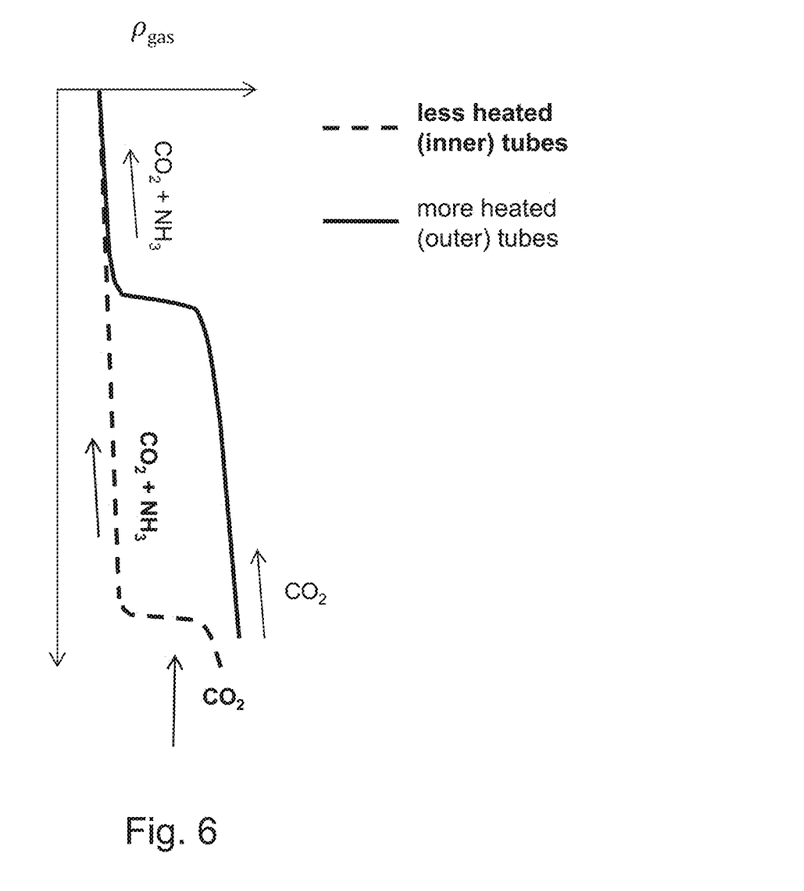
FIG. 6 is a schematic representation of gas density as a function of position in less-heated tubes and more heated tubes.

Also, the inventors discovered that in less heated tubes, carbamate decomposition occurs from the top of the tube until close to the bottom of the tubes, such that the entirety of the less heated tubes has a lower specific density compared to the more heated tubes, which in turn causes the hydrostatic pressure in the less heated tubes to be lower than the hydrostatic pressure in the more heated tubes. The gas density profile of the more heated outer tubes is shown in FIG. 5, panel a), left-hand graph. The gas density profile of the less-heated inner tubes is shown in FIG. 5, panel b), left-hand graph. The gas density profile in the less heated tubes and the more heated tubes is also compared in FIG. 6. FIG. 6 clearly shows that in the less heated tubes, carbamate decomposes near the bottom of the stripper compared to the more heated tubes. This results in a different density profile, which in turn causes a hydrostatic pressure difference. The lower hydrostatic pressure in the inner tubes causes the flow rate of the stripping gas in the less heated tubes to be higher than in the more heated tubes, which results in lower stripping efficiency.

This is slightly counteracted when $CO_2$ stripping gas with a lower temperature than the tubes is used, because the cooler $CO_2$ gas lowers the density of the gas phase in the tube, thereby increasing the hydrostatic pressure and counteracting the effect of the increased heating. However, this effect is not sufficiently pronounced to eliminate the stripping inefficiencies associated with inhomogeneous heating.

Indeed, simulations (results not included) showed that even a small difference in the density profile results in a significant effect on the flow distribution. In particular, the area-weighted average fluid flow velocity in the less-heated inner tubes was estimated to be ca. 5 times higher than the area-weighted averaged fluid flow velocity in the more heated outer tubes. This large discrepancy in fluid flow velocity results in significant stripping inefficiencies in prior art strippers.

In conclusion, inhomogeneous heating in sizable prior art $CO_2$ strippers results in corrosion issues and inefficient stripping. This problem can be solved by providing one or more additional heating fluid inlets between a first heating fluid inlet and a heating fluid outlet, thus allowing homogeneous heating such that all tubes of the stripper can be heated moderately and uniformly, which results in a low rate of corrosion throughout the stripper. In addition, the homogeneous heating results in a homogeneous gas density profile, which in turn results in a uniform stripping gas flow rate and improved stripping efficiency.

Example 7

In a further example, reference is made to FIG. 8, which shows three types of baffles (134,135,136) which can be used in the shell-side space of the present strippers.

In particular, panel a) shows segmental-type baffles (134). These baffles are arranged to obstruct alternating parts, e.g. diametrically opposed parts, of the shell-side space, thus forcing heating fluid to follow a sinuous path. In strippers with a circular cross section, each baffle obstructs the shell-side space bounded by a chord of the circular cross section and the major circle arc whose endpoints are the same as those of the chord.

Panel b) shows double-segmental type baffles (135) which feature two types of obstructions that are positioned alternatingly. For strippers with a circular cross section, the first type of obstruction features two plates that each block a diametrically opposed segment of the shell-side space, thus forcing heating fluid to flow through the centre of the shell-side space at their position. The second type of obstruction is a centrally disposed obstruction between two parallel chords, thus forcing heating fluid to flow near the sides of the shell-side space.

Panel c) shows disk-and-doughnut type baffles (136) which feature two types of obstructions that are positioned alternatingly. These types of baffles are used in strippers with a circular cross section. The first type of obstruction is a disk which is centrally disposed within the shell-side space, thus forcing heating fluid to flow near the sides of the shell-side space. The second type of obstruction is a doughnut-shaped plate. It obstructs fluid flow near the edges of the shell-side-space, and it has a hole that allows heating fluid to pass near the centre of the shell-side space.

The presence of baffles further improves the stripping efficiency and reduces tube corrosion by increasing the homogeneity by which the tubes are heated.

The invention claimed is:

1. A method for stripping a urea/carbamate mixture, the method comprising the steps:
   providing a shell-and-tube stripper,
      the stripper comprising a top end in fluid connection with a bottom end through a plurality of tubes disposed within a shell;
      the top end comprising an inlet for the urea/carbamate mixture and an outlet for a gas mixture comprising the stripping gas and one or more stripped compounds; and
   the bottom end comprising an outlet for a urea/carbamate stream concentrated in urea, and an inlet for a stripping gas,
      wherein the stripper further comprises a first heating fluid inlet, a second heating fluid inlet, and a heating fluid outlet being in fluid connection with a shell-side space disposed between the plurality of tubes and the shell; the first heating fluid inlet being adjacently disposed to the top end of the stripper and the heating fluid outlet being adjacently disposed to the rear end of the stripper; or the first heating fluid inlet being adjacently disposed to the bottom end of the stripper and the heating fluid outlet being adjacently disposed to the top end of the stripper; and
      wherein the second heating fluid inlet is disposed between the first heating fluid inlet and the heating fluid outlet, the second heating fluid inlet is positioned at a distance from the top end of the stripper that equals 35.0 to 75.0% of the distance between the top end and the bottom end of the stripper; and
   wherein the stripper comprises more than 3000 tubes;
   providing the urea/carbamate mixture to the inlet for the urea/carbamate mixture;
   providing a heating fluid to the shell-side space by means of the first heating fluid inlet, by means of the second heating fluid inlet, and optionally by means of the one or more further heating fluid inlets;
   contacting the urea/carbamate mixture and the stripping gas in a tube-side space disposed within the tubes, and heating the urea/carbamate mixture by means of the heating fluid, thereby obtaining a urea/carbamate stream concentrated in urea;
   extracting the urea/carbamate stream concentrated in urea at the outlet for the urea/carbamate stream concentrated in urea;
   extracting a gas mixture comprising one or more stripped compounds at the outlet for the gas mixture, the one or more stripped compounds comprising $NH_3$, $CO_2$, and water;
   extracting the heating fluid at the heating fluid outlet.

2. The method according to claim 1 additionally comprising the step of providing a stripping gas to the inlet for the stripping gas; wherein the gas mixture extracted at the outlet for the gas mixture further comprises the stripping gas.

3. The method according to claim 1 wherein the heating fluid consists of steam.

* * * * *